United States Patent [19]
Barath

[11] Patent Number: 6,165,176
[45] Date of Patent: Dec. 26, 2000

[54] APPARATUS FOR DISSECTING AND MOBILIZING ARTERIAL SEGMENTS FOR ESTABLISHING VASCULAR ANASTOMOSES

[76] Inventor: Peter Barath, 3 Hampton Dr., Oakbrook, Ill. 60523

[21] Appl. No.: 09/163,379

[22] Filed: Sep. 30, 1998

[51] Int. Cl.[7] ................................................. A61B 18/18
[52] U.S. Cl. ............................ 606/49; 606/159; 606/45
[58] Field of Search .................................. 606/41, 42, 45, 606/48, 49, 50, 159, 170

[56] References Cited

U.S. PATENT DOCUMENTS

| | | | |
|---|---|---|---|
| 5,460,629 | 10/1995 | Shlain et al. | 606/46 |
| 5,484,426 | 1/1996 | Toon | 604/286 |
| 5,540,683 | 7/1996 | Ichikawa et al. | 606/40 |
| 5,843,017 | 12/1998 | Yoon | 604/22 |
| 5,913,864 | 6/1999 | Garito et al. | 606/131 |
| 6,019,771 | 2/2000 | Bennett et al. | 606/159 |

*Primary Examiner*—Linda C. M. Dvorak
*Assistant Examiner*—Roy Gibson
*Attorney, Agent, or Firm*—Michael E. Klicpera

[57] ABSTRACT

A segment of an artery to be used, for example, in aortocoronary bypass surgery, is dissected and isolated by making an incision to sever the artery at one of the ends of the segment to be removed. Suturing means are employed to inhibit the flow of blood through the vessel segment. An interrupted collar/handle assembly is inserted at the incision and passed over the blood vessel so the segment is positioned within the luminal area of the collar. The collar has an inside diameter slightly larger than the outside diameter of the blood vessel to be isolated and has at least one cutting blade at its leading end. The collar is advanced over the blood vessel while the cutting edge is energized to sever tissue from the vessel and to cauterize ends of the severed branches, until the leading end of the collar reaches the desired length of segment, by which another incision is made to isolate the blood vessel.

13 Claims, 2 Drawing Sheets

APPARATUS FOR DISSECTING AND MOBILIZING ARTERIAL SEGMENTS FOR ESTABLISHING VASCULAR ANASTOMOSES

FIELD OF THE INVENTION

The present invention relates to apparatus and method for dissecting and mobilizing arterial segoments as a conduit to establish vascular anastomoses. More specifically, the present invention relates to an interrupted circular electrocauter cutting device attached to a tubular member for rapid dissecting and mobilizing of arteries with minimal injury to the blood vessel.

BACKGROUND OF THE INVENTION

It has been established that arterial conduits, specifically the internal mammary arteries (IMA), radial and gastroepipoic arteries are far superior to venous graft in bypassing diseased coronary arteries. The IMAs are in close proximity to the parietal pleura and small retrosternal muscles and generally are deeply embedded in connective tissue and surrounded by fat tissue. These arteries need to be dissected clean in order to be effectively mobilized. The numerous side branches require visualization for ligation/cauterization and adequate severance. The dissection and mobilization of the IMAs is a time consuming, delicate procedure during which a free mobile arterial segment must be formed to approach the surface of the heart where the target arteries are situated. At the same time, the structural integrity of the artery must be preserved to form a viable, long lasting bypass. The current procedure of mobilization can occur within thirty minutes if it is performed from a median sternotomy, however it may take much longer if it is performed from a limited access, such as a small lateral incision or thoracoscopy during minimally invasive procedures.

SUMMARY OF THE INVENTION

It is an objective of the invention to provide an improved device and rapid procedure with which a segment of an artery, specifically but not exclusively, the IMAs can be isolated and mobilized from the surrounding tissue and severed from their side branches. The initial procedure requires making a small incision through the parietal pleura and small retrosternal muscles over the distal segment of the IMA which allows sufficient length to obtain a non-stretched free conduit to form the bypass with the target coronary artery. A nominal 5 mm segment of the artery is dissected clear and exposed so that the collar/cutting edge assembly of the present invention can be positioned around the vessel to begin the isolation procedure. The assembly is an interrupted collar containing a substantially circular cutting edge embedded in heat and electrical insulator layers. The inner diameter of the assembly is to be selected approximately 1.0 to 1.5 mm larger than the outer diameter of the arterial segment to be isolated. The handle of the device is connected to a surgical electrocautery generator to be used during the routine part of the operation. The partially cleaned arterial segment is positioned into the collar/cutting assembly through the interrupting gap in a way that the non-insulated circular cutting edge is directed toward the proximal segment of the artery to be mobilized and the non-insulated cutting neck of the device between the handle and the collar be positioned at the plane of the parietal pleura. The handle of the device is positioned perpendicularly to the longitudinal axis of the arterial segment. The arterial segment distal to the positioned collar is ligated and held and slightly stretched with a pair of forceps. The electrocautery generator cutting mode is activated and the collar is cautiously advanced proximally with an approximate speed of 1 mm/sec holding the handle in such way that the new segments of the artery always remain positioned in the center of the collar and the handle remain perpendicular to the arterial axis. The generator is switched alternately between cutting and cautering modes. During the activation of the cutting mode, the collar/cutting assembly slowly cuts the artery circularly free from the surrounding connective tissue, parietal pleura and retrosternal muscles leaving a thin layer of the connective tissue surrounding the adventitia. During the cantering mode small diffuse bleeding is arrested and the major side branches are severed and cauterized. In this way, a free mobile segment of the IMA is obtained ready for establishing a conventional vascular anastomosis or using a modified anastomosis technique.

DESCRIPTION OF THE PREFERRED EMBODIMENT

Figure 1:
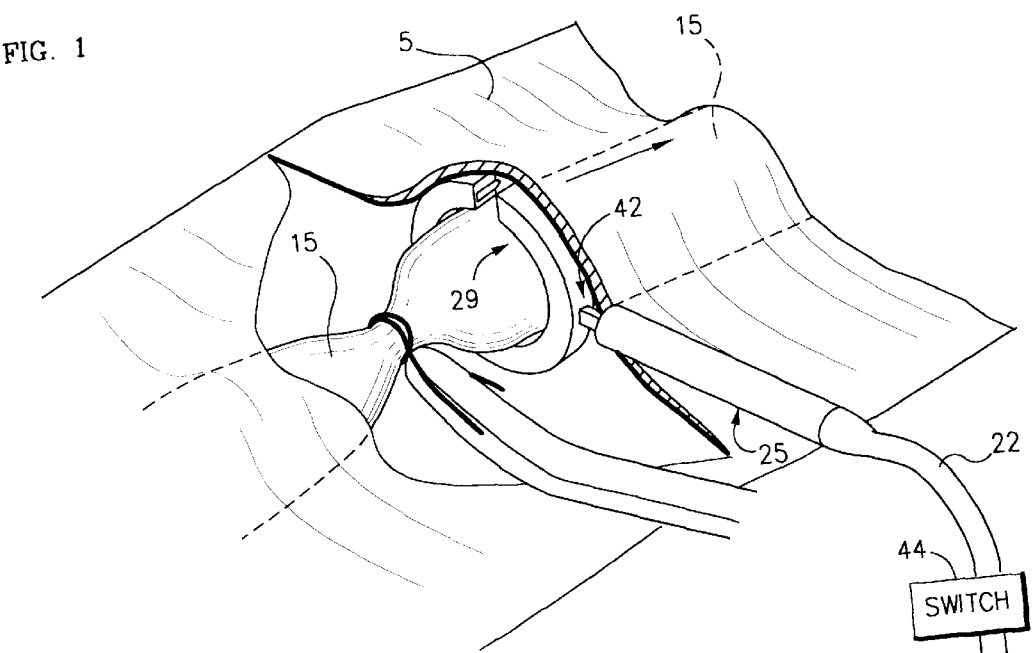
FIG. 1 is a perspective view of a surgical instrument in accordance with the present invention employed in its typical environment.

As illustrated by way of example in the drawings, apparatus in accordance with the invention comprises an elongate handle 25 with heat and electricity insulating properties and having an lengthwise transmission means 28 that engages a substantially circular blade 38 at junction 41. Located between the junction 41 and the handle, is a non-insulated neck 42 with cutting edge 45. Referring to FIG. 1, the present invention is shown positioned around an arterial segment 15. An electrocautery source 10 is engaged to the handle by means of cable 22. Once energized, the present invention is slowly moved in the direction of the arrows to sever the connective tissue 5 and isolate the blood vessel segment 15 from the perivascular tissue bed 20. A switch 44 can be provided anywhere along the length of the cable 22 to alternately select between the severing and cautering modes. As an artisan can appreciate, the switch can be a sliding, rotating, toggle or other design which simply breaks the contact along one of the wires located either within or near the handle.

Figure 2:
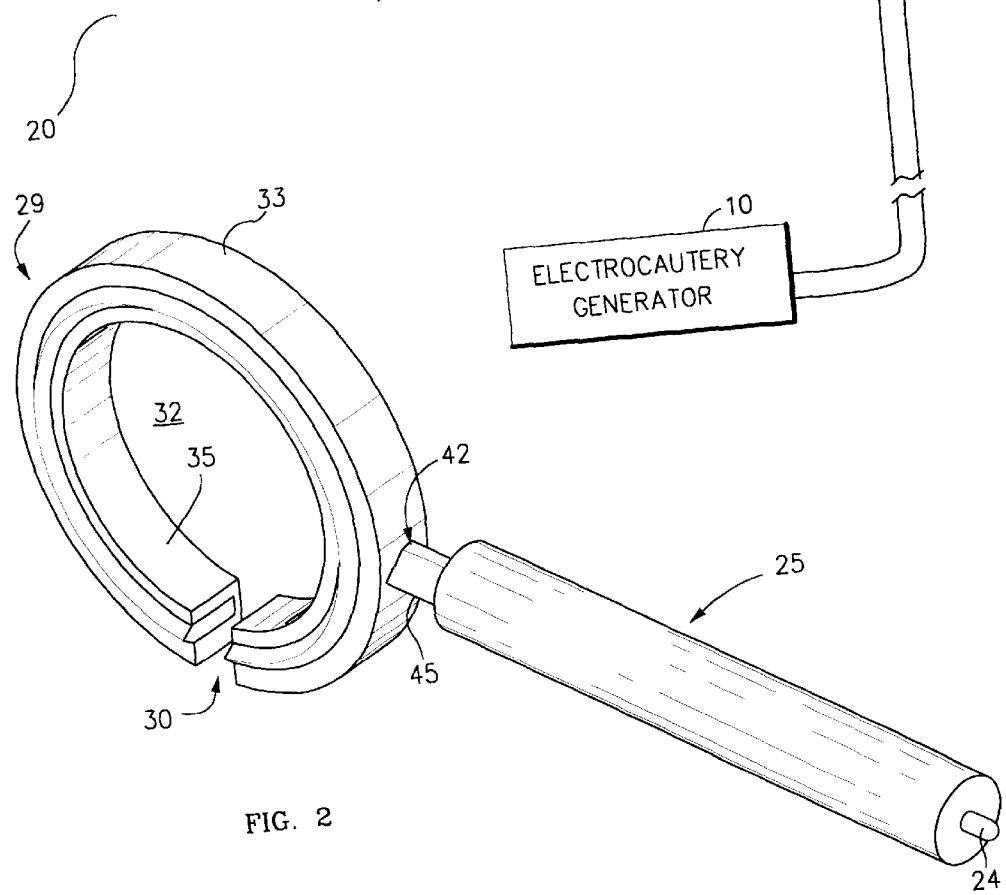
FIG. 2 is a perspective view of the present invention comprising an elongated tubular member having interrupted collar/circular cutting edge assembly mounted at the distal end.
Figure 3:
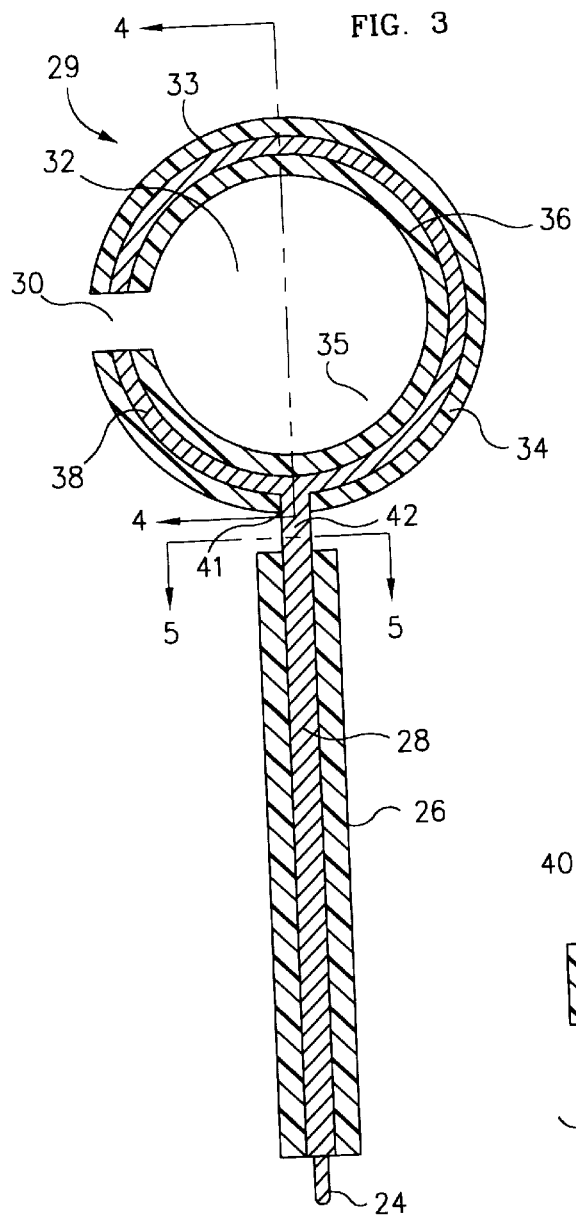
FIG. 3 is a cross-sectional side view of the present invention showing the substantially circular cutting edge partially embedded in the interrupted collar and engaged to a means to transfer electrical energy.

Now referring to FIGS. 2 and 3, a connector 24 is positioned at one end of the handle, herein referred to as the "proximal" end, for engagement with the cable 22. The electrocautery generator 10 is connected to the connector 24 on the handle 25 whereby connector 24 is engaged to a transmission means 28 running lengthwise with the handle. The transmission means 28 electrically engages connector 24 to the cutting neck 41 and the substantially circular blade 38. Electrocautery energy is supplied to energize the cutting edges 40 and 45 so as to facilitate dissection of tissue from the blood vessel to be mobilized and cauterize severed branches. The transmission means 28 of the handle 25 is appropriately sized for transferring electrocautery energy from a source 10 to the neck 42 and blade element 38. For this purpose, an electrical conductor is used, for example, either an insulated or non-insulated copper wire or preferably, a metallic rod element extending lengthwise either through or compromising the handle 25. The terminal end of the electrical conductor is connected to the cutting neck 42 with a suitable coupling mechanism. If a wire is employed, wire of sufficient diameter, ranging from 10 to 22 gauge with a preferable range being 14–18 gauge, could be used as the means for transferring electrocautery energy.

The handle 25 of the invention may have a length ranging from 2 to 14 inches, with the preferred length being determined by the appropriate application. For example, if the invention is used in an intra-operative setting the length might be considerable shorter than if employed otherwise, for example, in a thoroscopic setting where the handle length would preferably be at least 12 inches. The handle can be formed, for example, by extrusion or machining from a suitable plastic or metallic alloy and has sufficient strength to resist axial and torsional forces, being sufficiently rigid to inhibit bending. The handle can be fabricated from a suitable metal such as 300 or 400 stainless steel, Elgiloy or other suitable metallic material. If the handle comprises a non-conductive material, then the core must contain a conductive transmission means 28 such as a metallic rod or wire of sufficient gauge to transfer the electrocautery energy to the cutting neck 45 and circular cutting edge 38. The handle can be fitted with a jacket the surrounds the transmission means 28 that is comprised of a material that has a high electrical and heat resistance. Furthermore, the basic structure of the handle can be covered with a sleeve to provide additional insulation properties, or ergonomic and frictional characteristics to facilitate manipulation of the present invention. The jacket of the handle, for example, may be formed from electrically insulating material, such as thermoset plastics such as polysulfone, phenolic compounds, ceramics, Teflon, polyimid, Delrin or any other material which exhibits the other properties discussed above.

Figure 5:
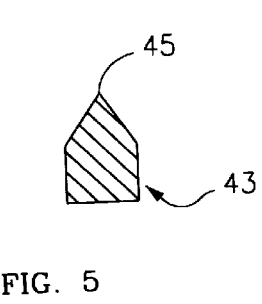
FIG. 5 is a cross-sectional view taken from the view 5—5 as demonstrated in FIG. 3, showing the cutting edge of the neck.
Figure 6:
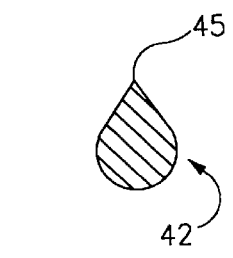
FIG. 6 is a cross-sectional view taken from the view 5—5 as demonstrated in FIG. 3, showing another cutting edge configuration of the neck.

At the other end of the handle, herein referred to as the "distal" end of handle 25, a substantially circular member or C-shaped collar 29 is mounted. Positioned between the collar and the handle is a neck 42 with cutting edge 45, also referred to herein as the cutting neck. The cutting neck 42 is firmly engaged to the cutting blade 38 and extends as a continuous element from the metallic rod comprising the transmission means 28. The length of the cutting neck 42 ranges approximately from 1 to 3 mm. It can be appreciated that the exact length of cutting neck 42 is not important, so long as functions to dissect the pariental pleura while the collar assembly is being advanced. Shown in FIGS. 5 and 6 are two embodiments of the cutting neck. In FIG. 5, the cutting neck 43 is configured as a pentagon with a cutting edge 45. In FIG. 6, the cutting neck 42 is tear drop shaped with cutting edge 45 located at the point.

Collar 29 is comprised of an inner circular section 36 which defines the periphery of luminal area or inside diameter 32, an outer circular section 34 and a substantially circular blade 38 with cutting edge 40. The collar is interrupted with a gap 30 to function as a means for introducing the blood vessel into the luminal diameter 32. The non-blade elements of collar 29 are preferably formed from a thermoplastic or ceramic material having high electrical resistance, heat insulation and flexibility characteristics. Since the substantially circular cutting edge 38 (and cutting neck 42) is energized with electrocautery energy, the material(s) of collar 29 must provide insulating properties to minimize any heat generated from the circular blade element from transferring to the collar's outer band 34 (and outer surface 33) and inner band 36 (and inner surface 35). It is also desirable that the collar materials exhibit lubricity characteristics so that the portion of the collar outer surface 33 that comes in contact with the connective tissue 5 and perivascular tissue 20 does not induce additional drag. Suitable materials for the non-blade elements (outer band 34 and inner band 36) are polyimide, polyamide, Teflon, ceramic, Delrin or polysulfone.

The outer band 34 defines an outer periphery 33 and can range from 0.5 mm to 1.5 mm in thickness, with a preferred range from 0.75 mm to 1.0 mm. It is desirable to minimized the thickness of the band, but depending on the materials of construction, a given thickness must be utilized to provide adequate insulation properties. The inner band 36 defines an inner periphery and therefore an inside diameter 32 and can range from 0.5 mm to 1.5 mm in thickness and preferably from 0.75 mm to 1.0 mm. It is desirable to minimized the thickness of the band, but depending on the materials of construction, a given thickness must be utilized to provide adequate insulation properties. Example of materials that the bands of the collar can be formed from are thermoplastic materials such as polysulfone, high density polyethylene, Teflon, or ceramic.

The collar is interrupted with a gap 30 to function as a means for introducing the blood vessel into the luminal diameter 32. As will be described in more detail hereinafter, blood flow is restricted before the present invention is utilized, and arteries devoid of blood are pliable and relatively thin. Gap 30 will range between 0.5 mm to 5.0 mm, with a preferable range of 1.0 mm to 2.5 mm, depending on the overall size of the circular collar and the particular application. Gap 30 must be large enough to allow a blood vessel to relatively slide through the gap and enter the luminal area 32. It can be appreciated that the exact size of gap 30 is not important, so long as functions to maintain the blood vessel with the luminal area 32 and is positioned such that the interrupted area is not necessary to cut connective tissue 5 and perivascular tissue 20 from the blood vessel to be isolated. It may also be desirable that the collar be somewhat flexible.

The present invention will also be available with numerous inside diameters or luminal areas 32 to approximately match the outside diameter of the artery or vein intended to be harvested. Since candidate blood vessels for harvesting generally have diameters between 0.5 mm to 5.0 mm, the luminal area 32 of the present invention will be available in varying sizes to match this clinical diversity. It is desirable for the inner diameter of the luminal area be approximately 1.5 mm larger than the diameter of the arterial segment to provide a thin layer surrounding the arterial segment when the dissection and isolation procedure is performed.

Figure 4:
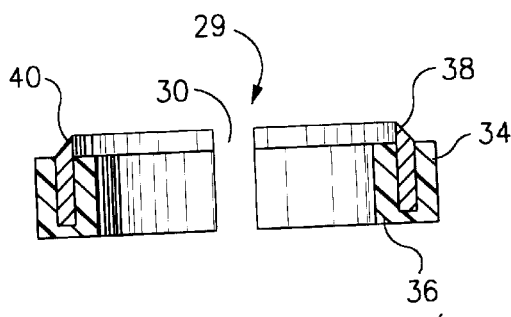
FIG. 4 is a cross-sectional view taken from the view 4—4 as demonstrated in FIG. 3, showing the cutting edge protruding from the collar.

Now refer to FIG. 4 which portrays a cross-sectional view of collar 29. The substantially circular cutting blade 38 is sandwiched between outer band 34 and inner band 36 and extends beyond both bands on the forward facing edge. The protruding blade is sharpened to yield a cutting edge 40 which facilitates the dissection of the blood vessel.

In order to avoid the cutting blade 38 from severing a segment of the artery that is not to be dissected and isolated, a mechanism (not shown) can be provided along the collar's 29 leading end to shield the cutting edge 40.

The procedure of removing an arterial segment with the instrument illustrated in FIGS. 1–6, is illustrated schematically in FIG. 1. FIG. 1 illustrates schematically the course of the arterial segment. The initial procedure requires making a small incision through the parietal pleura and small retrosternal muscles over the distal segment of the blood vessel which allows sufficient length to obtain a non-stretched free conduit to form the bypass with the target coronary artery. A small segment of the artery is dissected clear and exposed so that the collar/cutting edge assembly of the present invention can be positioned to surround the vessel to begin the isolation procedure. The assembly is an interrupted collar containing a substantially circular cutting edge embedded in heat and electrical insulator layers. The inner diameter of the assembly is to be selected approximately 1.0 to 1.5 mm larger than the outer diameter of the arterial segment to be isolated. The handle of the device is connected to a surgical electrocautery generator to be used during the routine part of the operation. The arterial segment is positioned into the collar/cutting assembly through the interrupting gap in a way that the non-insulated circular cutting edge is directed toward the proximal segment of the artery to be mobilized and the non-insulated cutting neck of the device between the handle and the collar be positioned at the plane of the parietal pleura. The handle of the device is positioned perpendicularly to the longitudinal axis of the arterial segment. The arterial segment distal to the positioned collar is ligated and held and slightly stretched with a pair of forceps. The electrocautery generator cutting mode is activated and the collar is cautiously advanced proximally with an approximate speed of 1 mm/sec holding the handle in such way that the new segments of the artery always remain positioned in the center of the collar and the handle remain perpendicular to the arterial axis. The generator is switched alternately between cutting and cantering modes. During the activation of the cutting mode, the collar/cutting assembly slowly cuts the artery circularly free from the surrounding connective tissue, parietal pleura and retrosternal muscles leaving a thin layer of the connective tissue surrounding the adventitia. During the cantering mode small diffuse bleeding is arrested and the major side branches are severed and cauterized. In this way, a free mobile segment of the IMA is obtained ready for establishing a conventional vascular anastomosis or using a modified anastomosis technique.

It will thus be seen that with the apparatus of the present invention, it is possible to remove a relatively long arterial section by making only incisions at opposite ends of the section to be removed.

I claim:

1. An apparatus for dissecting and isolating a blood vessel comprising:
    an interrupted collar having an inner surface, an outer surface, a back facing edge and a forward facing edge, said collar having a gap;
    a handle attached to the outer surface of said collar;
    transmission means extending lengthwise of said handle and engaged to a substantially circular cutting blade; and
    said substantially circular cutting blade at least partially embedded within said collar, a portion of said cutting blade extending forwardly beyond said forwardly facing edge, a portion of said cutting blade engaged to said transmission means.

2. An apparatus as recited in claim 1, further comprising a neck positioned between and engaged to said transmission means and said cutting blade, said neck having a cutting edge.

3. An apparatus as recited in claim 1, wherein said collar is sufficiently flexible to increase said gap to facilitate positioning of said collar assembly around a segment of said blood vessel.

4. An apparatus as recited in claim 1, further comprising a electrocautery source connected to a coupler engaged to said transmission means causing said cutting blade to increase from a first temperature to a second temperature.

5. An apparatus as recited in claim 3, further comprising a switch means for selectively connecting and disconnecting said electrocautery source.

6. A surgical instrument for isolating a blood vessel comprising:
    an elongated handle having a proximal and distal end,
    a substantially circular collar engaged to said distal end, said collar having a leading portion, said substantially circular collar having an interruption; and
    a severing means at a leading end portion of the collar for dissecting and cauterizing tissue from the blood vessel when the leading end of the collar is slipped over said blood vessel and forwardly advanced over and lengthwise along the blood vessel.

7. A surgical instrument as recited in claim 6 further comprising an energy means engaged to said severing means for facilitating dissection of tissue and isolation of the blood vessel.

8. A surgical instrument as recited in claim 7 further comprising a switch means for controlling the application of said energy means to said severing means.

9. A surgical instrument as recited in claim 6, wherein the severing means comprises at least one blade extending forwardly of the leading edge of the collar.

10. A surgical instrument as recited in claim 6, wherein the severing means further comprises a cutting edge extending forwardly of a leading end of a neck portion.

11. A surgical instrument as recited in claim 9, wherein the means for cauterizing comprises an electrically conductive portion of the blade, and such means connectable to a source of electrocautery energy during use of the surgical instrument for flowing electric current through the severing means thereby heating a cutting edge to cauterize branches.

12. A method of dissecting and isolating a blood vessel which comprises the steps of:
    restricting the supply of blood from a segment of a blood vessel,
    making a first incision at one end of a blood vessel severing a portion of said segment from a body tissue mass,
    positioning a dissecting and isolating apparatus with an inside diameter slightly larger then the diameter of said blood vessel, over an outer boundary of said blood vessel, such dissecting and isolating apparatus comprising a collar having a cutting edge with a neck portion having a cutting edge positioned between said collar and, a handle and a means for transferring electrocautery energy to said cutting edges; and
    advancing said dissecting and isolating apparatus along said blood vessel to dissect and mobilize said segment from said body tissues.

13. The method as recited in claim 12, further comprising the step of alternately applying cutting energy and electrocautery energy to said cutting edges.

* * * * *